United States Patent
Saku et al.

(10) Patent No.: US 10,653,785 B2
(45) Date of Patent: May 19, 2020

(54) COLLAGEN MATERIAL AND METHOD FOR PRODUCING COLLAGEN MATERIAL

(75) Inventors: Taro Saku, Yamatokouriyama (JP); Yoshihiro Isobe, Yamatokouriyama (JP); Takaoki Isobe, Yamatokouriyama (JP)

(73) Assignee: Atree, Inc., Tokyo (JP)

( * ) Notice: Subject to any disclaimer, the term of this patent is extended or adjusted under 35 U.S.C. 154(b) by 901 days.

(21) Appl. No.: 14/000,397

(22) PCT Filed: Feb. 20, 2012

(86) PCT No.: PCT/JP2012/001098
§ 371 (c)(1),
(2), (4) Date: Aug. 19, 2013

(87) PCT Pub. No.: WO2012/114707
PCT Pub. Date: Aug. 30, 2012

(65) Prior Publication Data
US 2013/0323199 A1 Dec. 5, 2013

(30) Foreign Application Priority Data
Feb. 21, 2011 (JP) ................. 2011-035239

(51) Int. Cl.
| | | |
|---|---|---|
| A61K 47/42 | (2017.01) | |
| A61L 27/54 | (2006.01) | |
| A61L 27/24 | (2006.01) | |
| A61K 9/00 | (2006.01) | |
| A61K 45/06 | (2006.01) | |
| A61F 2/14 | (2006.01) | |

(52) U.S. Cl.
CPC ............ *A61K 47/42* (2013.01); *A61K 9/0024* (2013.01); *A61K 45/06* (2013.01); *A61L 27/24* (2013.01); *A61L 27/54* (2013.01); *A61F 2/142* (2013.01); *A61L 2300/414* (2013.01); *A61L 2430/16* (2013.01)

(58) Field of Classification Search
CPC ...... C08L 67/00; C08L 2666/08; B32B 15/08; H05K 1/0353; Y10S 428/901; Y10T 428/10; Y10T 428/1086; Y10T 428/1095; Y10T 428/31786; A61F 2/142; A61K 45/06; A61K 47/42; A61K 9/0024; A61L 2300/414; A61L 2430/16; A61L 27/24; A61L 27/54; B01D 2259/40001; B01D 2259/40022; B01D 2259/403; B01D 2259/404; B01D 2259/4061; B01D 2259/4062; B01D 2259/4063; B01D 53/0438; B01D 53/0462
See application file for complete search history.

(56) References Cited

U.S. PATENT DOCUMENTS

| | | | |
|---|---|---|---|
| 5,308,889 A * | 5/1994 | Rhee | A61L 15/225 523/113 |
| 5,532,217 A | 7/1996 | Silver et al. | |
| 6,387,414 B1 | 5/2002 | Akashi et al. | |
| 2004/0037813 A1* | 2/2004 | Simpson | A61F 2/08 424/93.7 |
| 2004/0101960 A1 | 5/2004 | Schaefer et al. | |
| 2007/0031465 A1 | 2/2007 | Kojima et al. | |
| 2008/0033550 A1 | 2/2008 | Taira | |
| 2010/0074874 A1 | 3/2010 | Torbet et al. | |
| 2010/0166828 A1 | 7/2010 | Shoji | |

FOREIGN PATENT DOCUMENTS

| | | | |
|---|---|---|---|
| CN | 101554493 A | 10/2009 | |
| EP | 1902739 | 3/2008 | |
| JP | 10-127753 | 5/1998 | |
| JP | 11-319068 | 11/1999 | |
| JP | A 2000-271207 | 10/2000 | |
| JP | 2000-327314 | 11/2000 | |
| JP | 003408870 B2 * | 5/2003 | |
| JP | A 2003-301362 | 10/2003 | |
| JP | WO-2004-041320 | 5/2004 | |
| JP | 2005-278909 | 10/2005 | |
| JP | 2006-280222 | 10/2005 | |
| JP | A 2009-112569 | 5/2009 | |
| JP | WO 2009084507 A1 * | 7/2009 | ............ A61L 27/24 |
| JP | 2010-504122 | 2/2010 | |
| JP | 2010-148691 | 7/2010 | |
| JP | 2010-167274 A | 8/2010 | |

(Continued)

OTHER PUBLICATIONS

Chizuru Hongo et al., "Bunshi Haiko o Seigyo Shita Sekisoka Collagen Gel no Sosei," The Society of Polymer Science Japan, V. 37, 2008, p. 65-66.
Mitsuru Akashi et al., "Kakumaku Jisshitsu Saisei o Mokuteki to Shita Haiko Sekisogata Collagen Gel no Sosei," Kuntan Kenkyu Kakokkusho, 2008, pp. 9-12.
Y. Tanaka et al., "Fabrication of multilayered collagen hydrogels . . . ," Japanese Society for Biomaterials Symposium Yokoshu, 2008, vol. 2008, p. 138.
Chizuru Hongo et al., "Bunshi Haiko o Seigyo Shita Sekisoka Collagen Gel no Sosei to Kakumaku . . . ," Japanese Society for Biomaterials Symposium, 2008, vol. 2008, p. 139.
Masato Kukizaki et al., "Nano Bubble no Seisei to Kihokei no Seigyo," Miyazaki Pprefecture Industrial Technology Center, Hokoku, 2004, No. 48, pp. 13-16.

*Primary Examiner* — Lisa J Hobbs
(74) *Attorney, Agent, or Firm* — ALG Intellectual Property, LLC (57) ABSTRACT

A collagen material is characterized in being constituted of collagen gel fragments. Furthermore, the collagen gel fragments may have an orientation. A method for producing a collagen material is characterized in comprising a step for preparing collagen gel fragments, a step for arranging the collagen gel fragments in a desired shape, and a step for drying the collagen gel fragments arranged in the desired shape. Moreover, in one embodiment of the method for producing a collagen material a step may include imparting an orientation to the collagen gel fragments.

4 Claims, 7 Drawing Sheets

(56) References Cited

FOREIGN PATENT DOCUMENTS

| JP | 2012-500203 | 1/2012 |
|---|---|---|
| WO | WO-2001037889 | 5/2001 |
| WO | WO-2005035014 | 4/2005 |
| WO | WO-2008-034854 A1 | 3/2008 |
| WO | WO-2008-157594 | 12/2008 |
| WO | WO-2009-084507 | 7/2009 |
| WO | WO-2010-019625 | 2/2010 |
| WO | WO-2010-095427 | 8/2010 |
| WO | WO-2010-101639 | 9/2010 |

OTHER PUBLICATIONS

Tetsushi Taguchi et al., Hydroxyapatite Formation on/in Poly(vinyl alcohol) Hydrogel Natrices Using a Novel Alternate Soaking Process, Apr. 16, 1998.

Masanori Kikuchi et al., Self-organization mechanism in a bone-like hydroxyapatite/collagen nanocomposite synthesized in vitro and its biological reaction in vivo, Oct. 8, 2000.

Tadashi Shinohara et al., The Journal of Physical Medicine, Nov. 30, 2008, vol. 19.

Taro Takeuchi et al., Abstracts of the Japan Institute of Metals, Sep. 15, 2009, vol. 145th.

Y. Yokogawa et al., Calcium Phosphate Formation on Highly-oriented Collagen Fibrls, Chem. Lett, No. 6, Jun. 5, 1999.

Aira Matsugaki et al, Abstracts of the Japan Institute of Metals, Sep. 25, 2010, vol. 147th.

Jim Torbet et al., Orthogonal scaffold of magnetically aligned collagen lamellae for corneal stroma reconstruction, Mar. 6, 2007.

Chizuru Hongo et al., Development of Collagen Hydrogel with High Mechanical Strength by a Simple Orientation Method for Triple-helix, Chemistry Ltrs, vol. 37, No. 12, p. 1254-1255.

Mitsuru Akashi et al., "Kakumaku Jisshitsu Saisei o Mokuteki to Shita Haiko Sekisogata Collagen Gel no Sosei," Kuntan Kenkyu Kokokkusho, 2008, pp. 9-12.

Joselito Razal et al., Arbitrarily Shaped Fiber Assemblies from Spun Carbon Nanotube Gel Fibers, 2007.

Search Report and Written Opinion received in International Application No. PCT/JP2012/001098; dated Jun. 5, 2012.

Chizuru Hongo et al., "Bunshi Haiko o Seigyo Shtta Sekisoka Collagen Gel no Sosei to Kakumaku . . . " Japanese Society for Biomaterials Symposium, 2008, vol. 2008, p. 139.

EA Office Action, dated Dec. 4, 2014, issued in related Patent Application No. PCT/JP2011/005203.

* cited by examiner

COLLAGEN MATERIAL AND METHOD FOR PRODUCING COLLAGEN MATERIAL

TECHNICAL FIELD

The present invention relates to a collagen material, and a method of producing the collagen material, in particular, a collagen material and a method of producing the collagen material, using a collagen segment.

BACKGROUND

In the past, a non orientated collagen was used as a substrate material of a cell culture for many years. On the contrary, a collagen having an orientation is found in tremendous numbers in the human body according to the site, and therefore, it is extremely important to design and produce a shape and a direction of the orientation of the collagen material in a field of regeneration medicine etc., without any inhibition.

As a method of a collagen substrate having an orientation, it is generally known a method of applying a powerful magnetic field to it during a process of formation of a collagen fiber ("Patent Literature 1"). Further, it is also known a method of spin-coating a collagen gel ("Patent Literature 2").

PRIOR LITERATURE

Patent Literature
Patent Literature 1: JP-A-2006-280222
Patent Literature 2: JP-A-2010-148691

DISCLOSURE OF THE INVENTION

Problems to be Resolved by the Invention

However, in a method of producing a collagen material as described in the above Patent Literatures 1 and 2, it was impossible to allow a planar shape or a three-dimensional shape such as a ribbon, a sheet, a tube, a block to be freely set, and allow direction of orientation in the material to be freely set.

Moreover, although there is a technique for orientation of a collagen, there are no technique for designing a shape of collagen material and a direction of orientation in the material freely. As a result of this, there are only non orientated and an orientated collagen material having a limited shape and a limited direction of orientation.

Therefore, it is an object of the present invention to provide a method of producing an oriented collagen material which makes it possible to design a shape and a direction of orientation freely, and an oriented material obtained by the method.

Means of Solving the Problems

In order to accomplish the above object, the present inventors made strenuous studies as to a collagen material using both a collagen having orientation and non orientated collagen.

That is, a collagen material according to the present invention, is characterized in that the material comprises a collagen gel fragment.

Furthermore, in a preferred embodiment of the above mentioned collagen material according to the present invention, the material is characterized in that the collagen gel fragment has orientation.

Furthermore, in a preferred embodiment of the above mentioned collagen material according to the present invention, the material is characterized in that the collagen gel fragment has no orientation.

Furthermore, in a preferred embodiment of the above mentioned collagen material according to the present invention, the material is characterized in that the collagen gel fragment comprises both the collagen gel fragment having orientation and the collagen gel fragment having no orientation.

Furthermore, in a preferred embodiment of the above mentioned collagen material according to the present invention, the material is characterized in that a shape of the collagen gel fragment comprises at least one selected from the group comprising a string, a ribbon, a sheet, a sponge, a grain, a rod, a ring, a spiral, a spring, a disk, a dome or a block.

Furthermore, in a preferred embodiment of the above mentioned collagen material according to the present invention, the material is characterized in that the orientation is an uniaxial orientation, a spiral orientation, a double axis orientation, a two-dimensional orientation, a triaxial orientation, or a three-dimensional orientation.

Furthermore, in a preferred embodiment of the above mentioned collagen material according to the present invention, the material is characterized in that a part or all of the collagen gel fragment is coated on a substrate comprising metal, ceramics, high-polymer material or biomaterial.

Furthermore, in a preferred embodiment of the above mentioned collagen material according to the present invention, the material is characterized in that the collagen gel fragment includes a cell growth promotant.

Furthermore, in a preferred embodiment of the above mentioned collagen material according to the present invention, the material is characterized in that the cell growth promotant is Epidermal growth factor (EGF), Insulin-like growth factor (IGF), Transforming growth factor (TGF), Nerve growth factor (NGF), Brain-derived neurotrophic factor (BDNF), Vesicular endothelial growth factor (VEGF), Granulocyte-colony stimulating factor (G-CSF), Granulocyte-macrophage-colony stimulating factor (GM-CSF), Platelet-derived growth factor (PDGF), Erythropoietin (EPO), Thrombopoietin (TPO), basic fibroblast growth factor (bFGF or FGF2), or Hepatocyte growth factor (HGF).

Furthermore, in a preferred embodiment of the above mentioned collagen material according to the present invention, the material is characterized in that a shape of the material is a ribbon, a sheet, a tube, a sponge, a grain, a rod, a ring, a spiral, a spring, a disk, a dome or a block.

Furthermore, in a preferred embodiment of the above mentioned collagen material according to the present invention, the material is characterized in that the material is designed so as to become almost equal to the orientation of each site of a normal tissue from a living organism.

Furthermore, in a preferred embodiment of the above mentioned collagen material according to the present invention, the material is characterized in that the material contains oxygen.

Furthermore, a method of producing a collagen material according to the present invention, a method is characterized in that a method comprises;
a step for preparing a collagen gel fragment,
a step for arranging the collagen gel fragments in a desired shape, and a step for drying the collagen gel fragments arranged in the desired shape.

Furthermore, in a preferred embodiment of the above mentioned method of producing a collagen material according to the present invention, a method is characterized in that a method further comprises;
a step for imparting an orientation to the collagen gel fragments.

Furthermore, in a preferred embodiment of the above mentioned method of producing a collagen material according to the present invention, a method is characterized in that the desired shape is planar shape and/or three-dimensional shape.

Furthermore, in a preferred embodiment of the above mentioned method of producing a collagen material according to the present invention, a method is characterized in that the desired shape is a ribbon, a sheet, a tube, a sponge, a grain, a rod, a ring, a spiral, a spring, a disk, a dome or a block.

Furthermore, in a preferred embodiment of the above mentioned method of producing a collagen material according to the present invention, a method is characterized in that the step for drying the collagen gel fragments is carried out by freeze dry.

Furthermore, in a preferred embodiment of the above mentioned method of a collagen material according to the present invention, a method is characterized in that the method further comprises;
a step for introducing bubble into the collagen gel fragment, by means of any one method of a pressure-reduced pressure method, a gas-liquid shearing method and/or a method of introducing bubble using a membrane having a pore.

Moreover, a collagen material according to the present invention is characterized in that the material is obtained by the method of producing a collagen material according to the above present invention.

Effect of Invention

The present invention has an advantage effect that it is possible to design a shape and a direction of orientation as to an orientated collagen material freely. Further, the present invention has an advantage effect that it is possible to produce a biocompatible material which an orientation is controlled so that the orientation can be nearly equal to an orientation of each site of a normal tissue of a living organism, and further to put into practice regeneration of normal tissue of a living organism, since it is possible to produce a material having an orientation of collagen according to a site in a tissue from a living organism.

The present invention has an advantage effect that it is possible to produce a collagen material at a macro size of a millimeter order or more. Moreover, the method of producing a collagen material according to the present invention has an advantage that it is easy to manufacture and it is possible to produce a collagen material capable of being designed their shape freely. Further, the present invention has an advantage effect that if an orientated collagen with a string shape is aligned to a desired direction in a plane shape or a three-dimensional shape, it is possible to design a direction of orientation in the collagen material freely.

Furthermore, the present invention has an advantage effect that even if a dried orientated or non orientated collagen material is immersed into PBS or cell culture medium etc, or is implanted into the living body, the shape of the material is maintained for necessary period and is not dissolved to the original shape of the collagen gel fragment such as a string shape etc. The reasons why the shape of the material is maintained for necessary period and it is difficult to dissolve, is assumed that according to a triple-strand helix conformation which is one of feature of collagen molecule, a hydrophobic residue is thrown out to outside to make their residues assemble and be firmly fixed.

BRIEF DESCRIPTION OF THE DRAWINGS

FIG. 3(b) shows those that an orientated collagen gel with a string shape is aligned and after that being dried, and FIG. 3 (c) shows those of the end of the dried orientated collagen gel being cut.

MODE FOR CARRYING OUT THE INVENTION

A collagen material according to the present invention comprises a collagen gel fragment. That is, a collagen material of the present invention is a collagen material comprising one or more collagen gel fragment(s). In the past, in the case that a collagen material is prepared, a powdered state of collagen is dissolved in solution to prepare collagen solution, the collagen solution is used as a state substance, and the collagen solution is gelated by a gelatinizing agent etc., to obtain a desired sheet. On the other hand, in the present invention, it is possible to obtain a collagen material by preparing a collagen gel fragment as a start substance, and then coupling each collagen gel fragments as mentioned above. The coupling of each collagen gel fragments may be carried out by using a gelatinizing agent etc. Further, as one of the feature of the present invention, it is possible to carry out the coupling of each collagen gel fragment without using a specific gelatinizing agent. That is, it is possible to align the collagen gel fragment in a desired shape, and to dry and fix it to couple each collagen gel fragments.

A collagen is included in every tissue in the body such as skin, muscle, internal organ, bone. A collagen is different from other protein, and makes structure made by fiber or membrane in a space between a cell and a cell, that is, in outside of a cell. Almost collagen exists as an insolubility substance. That is, it is thought that in the living body, a collagen plays a role in something like a binder capable of coupling a cell and a cell, and as well as plays a role in a barrier for aligning a cell in a correct position. That is, a collagen makes it possible to make, serve as a backbone of and couple the conformation of every part of the body, internal organ etc., to make borderline between a cell. The collagen is so called as a cell matrix.

A collagen molecule has about 300 nanometer of length, about 1.5 nanometer in diameter, and a shape of a rod, and the molecule has a triple-strand helix structure (helix structure) wherein three chains twist together with each other. The collagen molecule is coupled with each other with connecting bridges thereof to increase the intensity of coupling. As a feature of the collagen molecule, it has a property that it will be solved by heat, this is an opposite feature comparing with a general protein having a feature that it will be solidified by heat. In general, so called gelatinization means that three chains come loose to divide into a single strand. A temperature capable of generating the change is generally called as a denaturation temperature, it is about 40° C. or more in a collagen of the land-dwelling creature, it is about 0 to 25° C. in a collagen of the heterothermic animal.

In the present invention, it is possible to obtain a collagen material wherein a collagen gel fragments are coupled with each other. Although details of their mechanism is unclear, since it is possible to set in a desired shape and to be solidified by drying, it is thought that the regeneration of each collagen gel fragment makes it possible to couple and stabilize them without using a gelatinizing agent. Moreover, a step for drying may be general natural seasoning or freeze drying.

Furthermore, in a preferred embodiment of the above mentioned collagen material according to the present invention, the collagen gel fragment has orientation. At this moment, a simple explanation as to the orientation is as follows.

First of all, an explanation as to a collagen having an orientation is as follows. A collagen having an orientation means a collagen which a travel direction of a fibrous collagen such as a single collagen gel or a dry collagen gel uniforms in some direction. In the case that a collagen having an orientation is coated in a substrate comprising a metal, a ceramics, a high-polymer material or a biomaterial (hereinafter it is a collagen substrate), a collagen having an orientation means a collagen which a travel direction of a fibrous collagen such as a single collagen gel or a dry collagen gel coated on a substrates such as a metal, a ceramics, a high-polymer material or a biomaterial formed to various shapes, uniforms in some direction.

An advantage of the use of a collagen gel having an orientation as a starting material is as follows. That is, the reasons are that the use of a collagen having an orientation in a curve within a collagen as a stating material makes it possible to also produce an orientation in a curve in an osteoblast. Further, in the present invention, it is essentially possible to develop an osteoblast with an orientation at a "surface" of collagen (substrate), although it is also thought that an osteoblast gets into inside of a collagen (substrate), it is possible to include such cases in the present invention. Furthermore, according to the present invention, if an orientated collagen gel having some shape and some direction of an orientation as a starting material is prepared depending on a needs of an orientated material as an end product, it is possible to produce an orientated collagen material with a larger size than a millimeter order by controlling a shape or a direction of an orientation without any inhibition.

A method of preparing a collagen gel having an orientation is not particularly limited, but according to a common procedure. For example, as a method of imparting an orientation to a collagen gel at a larger size than a millimeter order, a method of giving a flow of a fixed direction to collagen solution during a process of gelating a collagen solution is suggested, but other method may be used. As other method, mention may be made of a method of applying a strong magnetic field during a process of forming a collagen fiber, a method of spin-coating a collagen gel, a method of drawing a collagen gel to a predetermined direction mechanically (and physically).

In the case that a collagen gel fragment having an orientation is prepared by a method of applying a strong magnetic field during a process of forming a collagen fiber, since a collagen fiber is set in array in a perpendicular direction to the magnetic field, if it is kept to apply a magnetic field from the same direction, it is possible to obtain a two-dimensional orientation, and if it is kept to apply a rotational magnetic field, it is possible to obtain a single axis orientation. It is possible to use a method of applying a magnetic field if such collagen gel having an orientation is used as a starting material. However, if the magnetic field is used, basically, it is possible to produce only those of the collagen having a uniform orientation, and a macro shape also tends to be limited. On the other hand, in the case that a collagen gel having an orientation is prepared by a method of giving a flow of a fixed direction to collagen solution during a process of gelating a collagen solution. it is possible to produce a collagen having a different 3D orientation by forming and laminating a various shape including a sheet-like shape because of the use of a flow of liquid.

In such method, an orientated collagen (single collagen) in the example can be obtained by using a flow of a collagen solution to give an orientation to a collagen during a process of obtaining a collagen gel. Although it is a string-shaped of a collagen in the photograph of the example, it is possible to produce an orientated collagen gel or a collagen gel fragment with various shapes (line, plane, three dimension) such as a ribbon-shaped with a large width. Further, during a process, a control of a velocity of a flow also makes it possible to control a degree of the orientation. Therefore, since it is possible to control a direction of the orientation or a degree of the orientation thereby giving a desired distribution even if it is in the same collagen gel, the use of such collagen gel or collagen gel substrate according to the present invention also makes it possible to control a direction of the orientation and a degree of the orientation (that is control of distribution of the orientation). Moreover, controlling of the orientation manly includes two meaning: At first, (1) it is possible to make an orientation to the collagen material itself freely, and (2) it is possible to control a growth of a cell and a tissue on the line with an orientation of the collagen material in the case that a cell is cultured by using the collagen material having those orientation, or in the case that a living tissue is regenerated. In the present invention, it is possible to control these two orientations as mentioned above.

For example, an explanation as to a method of giving a flow of a fixed direction to collagen solution during a process of gelating a collagen solution is as follows. Although a concentration of a collagen solution is preferably 10 mg/mL or more from a viewpoint that an obtained collagen or a collagen substrate can have an enough mechanical strength, it may be about 3 mg/mL or more. An origin of a collagen is not limited. Further, a seed, a site of a tissue, an age etc., of an animal derived from are not particularly limited. For example, it is possible to use one derived from animals such as a rat tail, a pig hide, a cowskin, a camel bird, a fish. That is, it is possible to use a collagen obtained from a skin, a bone, a cartilage, a tendon, an internal organ of a mammal (for example, such as a cattle, a pig, a horse, a rabbit, a mouse etc.) or birds (for example, chicken etc.). A collagen like protein derived from a skin, a bone, a cartilage, a fin, a fish scale, an internal organ of fishes (for example, such as a pacific cod, a paralichthys olivaceus, a flatfish, a salmon, a trout, a tuna, a chub mackerel, a sea bream, a sardine, a shark etc.) may be used. Moreover, a method of extracting a collagen is not particularly limited, but a common method of extracting may be used. Further, a collagen obtained by a recombinant DNA technique other than that from the extraction from an animal tissue, may be used. Further, in order to suppress an antigenicity, an enzyme-treated atelocollagen may be used. Further, as a collagen, an unmodified soluble collagen such as an acid soluble collagen, a salt soluble collagen, an enzyme soluble collagen (atelocollagen), a chemically-modified collagen such as acylation such as succinylation, phthalation, esterification such as methylation, deamination of alkali solubilization, and further an insoluble collagen such as a tendon collagen etc., may be used. Further, a chemical cross-linking agent, a medicinal agent or an air bubble such as oxygen may be introduced into a collagen solution. A method of introducing them is not particularly limited, but according to a common procedure.

It is possible to quantitatively assess a direction of orientation or a degree of orientation as to an obtained collagen by using, for example, a raman spectroscopy microscope. A raman spectroscopy is to examine a component which a frequency modulation of a scattered light caused by hitting against molecular is occurred according to molecular vibration, by means of the use of a spectroscope, and thereby making it possible to obtain information as to composition of a target for analysis or a crystal structure to analysis an orientation of collagen.

Furthermore, in a preferred embodiment of the above mentioned collagen material according to the present invention, the collagen gel fragment has no orientation. Because even if the collagen gel fragment having no orientation is used as a stating material, it is possible to obtain a collagen material by means of aligning the collagen gel fragment in a desired shape to dry and be firmly fixed. Furthermore, in a preferred embodiment of the above mentioned collagen material according to the present invention, is characterized in that the collagen gel fragment comprises both the collagen gel fragment having orientation and the collagen gel fragment having no orientation. A method of producing the collagen gel fragment having no orientation is not particularly limited, but according to a common procedure. It is possible to obtain the collagen gel fragment having no orientation if the step for giving an orientation is omitted in the above method of producing the collagen gel fragment having orientation.

Moreover, in the above, although the collagen gel fragment with a string shape is mainly explained, in a preferred embodiment of the above mentioned collagen material according to the present invention, a shape of the collagen gel fragment may comprise at least one selected from the group comprising a string, a ribbon, a sheet, a sponge, a grain, a rod, a ring, a spiral, a spring, a disk, a dome or a block.

Furthermore, in the case that it will be explained from a viewpoint of the control of orientation, it is possible to control a direction of orientation and a degree of orientation of the collagen material by means of controlling a direction of orientation and a degree of orientation of the collagen gel or the collagen gel fragment.

Furthermore, in a preferred embodiment of the above mentioned collagen material according to the present invention, is characterized in that the orientation is an uniaxial orientation, a spiral orientation, a double axis orientation, a two-dimensional orientation, a triaxial orientation, or a three-dimensional orientation.

Furthermore, in a preferred embodiment of the above mentioned collagen material according to the present invention, a part or all of the collagen gel fragment is coated on a substrate comprising metal, ceramics, high-polymer material or biomaterial. Moreover, a method of coating is not particularly limited, but according to a common procedure. Further, in the present invention, it is one of the future that the above collagen material is a macro size at a larger size than a millimeter order.

Furthermore, in a preferred embodiment, from a view point that a cell grow up for a short period to accelerate the regeneration of tissue, the collagen gel fragment includes a cell growth promotant. As the cell growth promotant, mention may be made of Epidermal growth factor (EGF), Insulin-like growth factor (IGF), Transforming growth factor (TGF), Nerve growth factor (NGF), Brain-derived neurotrophic factor (BDNF), Vesicular endothelial growth factor (VEGF), Granulocyte-colony stimulating factor (G-CSF), Granulocyte-macrophage-colony stimulating factor (GM-CSF), Platelet-derived growth factor (PDGF), Erythropoietin (EPO), Thrombopoietin (TPO), basic fibroblast growth factor (bFGF or FGF2), or Hepatocyte growth factor (HGF), or one or more combination thereof.

Figure 1:
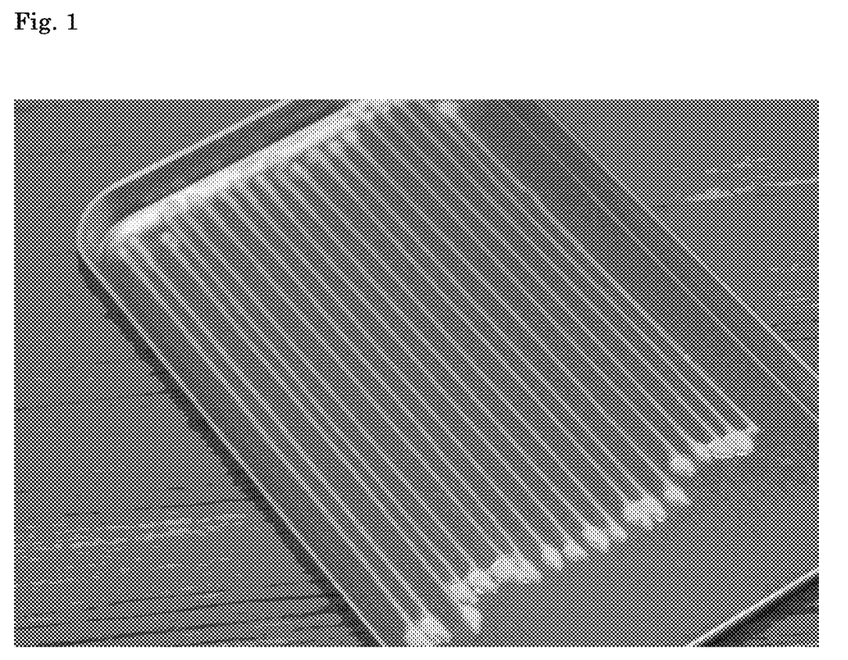
FIG. 1 gives a photograph of an orientated collagen gel with a string shape immediately after it is produced in PBS.

Furthermore, in a preferred embodiment of the above mentioned collagen material according to the present invention, a shape of the material is a ribbon, a sheet, a tube, a sponge, a grain, a rod, a ring, a spiral, a spring, a disk, a dome or a block. These can be prepared by a manner of orientation of the above collagen gel fragment, or a process after aligning it to dry and be firmly fixed. It is possible to carried out a secondary process as to the collagen material consisting of the collagen gel fragment of the present invention. That is, it is possible to prepare a sheet type of collagen material (fragment) from a string shape as shown in FIG. 1 and to further process the collagen material to make a many sort of a final shape type of the three dimensional collagen material.

Furthermore, in a preferred embodiment, the material is characterized by being designed so as to become almost equal to the orientation of each site of a normal tissue from a living organism. The collagen material designed so as to become almost equal to the orientation of each site of a normal tissue from a living organism can be used as a material for the regeneration medicine without modification.

In the present invention, it is possible to basically produce a dry type of the collagen material. However, it is also possible to produce gel type of the collagen material, for example, obtained by immersing a dry type of the collagen material into PBS etc. In general, although a part of tissue of the collagen material may be destroyed if it is dried, the dry type of material will be easy to use from a view point of storage stability (it is easy to maintain a shape. A gel is easy to corrupt since it contains water.), transit performance (A gel is easy to destroy since it contains water. It may become deformed when it is took up from a vessel.)

In the present invention, a dry type of the collagen material can be used as a gel type of the collagen material by setting back it to a gel with PBS, medium when using it actually. In the present invention, a dry type of the collagen material become increased in density of collagen fiber tissue by drying to drop out of water from a gel (It contains 90% or more of water.). Even if it is set back to a gel with PBS or medium again, it will be a small size in volume comparing with an original dried collagen material. As a result of this, the dry type of the collagen material has a lot of advantage, such as strength or orientation comparing with those of a gel type when manufactured, since an increase in density of the tissue remains.

In such manner, as one of a feature in the present invention, it is possible to produce a dry type of the collagen material as well as a gel type of the collagen material by setting back it to a gel with PBS or medium.

Furthermore, in a preferred embodiment of the above mentioned collagen material according to the present invention, the material is characterized by containing oxygen. In the collagen material, an advantage of containing oxygen is as follows. That is, in the case that the collagen material contains oxygen, it is though that there are a few merit, such as (a) it become a resource of air (oxygen) to a cell in the case that a cell grows up in inside of the collagen material, and further (b) it gives a space making it possible to grow up a cell into inside of the collagen material.

Although oxygen may include bubble, an embodiment of containing oxygen will be explained as follows. That is, containing of oxygen may be nearly equal to containing bubble. As the component, (1) in the case that it contains air (which is general air containing oxygen, nitrogen, carbon dioxide), (2) in the case that a low concentration or a high concentration of oxygen is contained in air (which also includes those of the content of the other components such as nitrogen or carbon dioxide being changed depending on increase and decrease of oxygen concentration.), (3) in the case that it contains only oxygen. It is though that there are at least the above three embodiments of containing oxygen.

A method which once a collagen gel fragment is dried may be a general method for using since there is a possibility that a collagen gel fragment is difficult to couple each multiple collagen gel fragment and thereby is difficult to become a stable and complicated shape of a collagen material, and easy to separate these fragments.

If the collagen is dried, it is a fiber. However, a collagen sheet has a feature which is not easy to pass water. Therefore, all of the introduced bubble is not blown up as gas. A part of at least oxygen and bubble remains to be trapped in inside of the collagen material even if it is dried.

If a bubble is introduced into a collagen solution and a content of the collagen solution increases from 100 to 110, 10 of a ration of the bubble will be remained. However, it is though that some part of a bubble is blown up during a dry process of the collagen material. Although if the collagen gel is not dried, almost all contents of the bubble which is introduced into the collagen solution is fixed in the collagen gel, the contents of the bubble which is blown up, and which remains in the gel during a dry process will be case by case. if there is 100 of the collagen solution and 1% of the concentration of collagen, 99% is water. It is thought that some extent of bubble will be blown up together with the 99% of water.

Next, a method of producing the collagen material of the present invention will be explained. The method of producing the collagen material of the present invention comprises;

a step for preparing a collagen gel fragment,
a step for arranging the collagen gel fragments in a desired shape, and a step for drying the collagen gel fragments arranged in the desired shape. A step for drying the collagen gel fragments may be include both general natural seasoning and freeze dry. An explanation as to a collagen gel fragment can be directly applied to and referred to the example using the collagen gel fragment in the explanation of the above collagen material according to the present invention. It is possible to align a collagen gel fragment in the line with a shape etc., of a final product collagen material, and dry the collagen gel fragment and thereby coupling the collagen gel fragment each other, and finally obtaining the collagen material consisting of the collagen gel fragment. Moreover, it is difficult to check a boundary of the collagen gel fragment with eyes after the collagen gel fragments are dried and coupled each other.

Furthermore, in a preferred embodiment, the step for drying the collagen gel fragments may be carried out by freeze dry. Although there are the above merits in the case of a natural seasoning, by contrary, it is thought that the volume of the fragment become reduced in size comparing with the original fragment, and thereby getting smaller a space for growing up a cell into an inside of the collagen material. It is possible to avoid these problems in the case of freeze dry. That is, in the case of freeze dry, it is possible to produce a collagen gel fragment and after that, to fixed with each fragments and maintain a condition that the inside of the fragment, as a result, the inside of all the produced fragment become hollowed out. By doing this, it is easy to grow up a cell into inside of the collagen material.

Furthermore, in a preferred embodiment, is characterized in that the method further comprises;

a step for arranging an orientation to the collagen gel fragment. A method for preparing an orientation to the collagen gel fragment is not particularly limited, but according to a common procedure. For example, it is possible to apply to the above method of producing the orientated collagen gel fragment, in the case of giving an orientation to the collagen gel fragment. That is, mention may be made of a method of using the above collagen solution, a method of using a magnetic field, and a method of spin-coating a collagen gel, and it is not particularly limited.

Furthermore, in a preferred embodiment, a method is characterized in that the desired shape is planar shape and/or three-dimensional shape. Specifically, as the desired shape, mention may be made of a ribbon, a sheet, a tube, a sponge, a grain, a rod, a ring, a spiral, a spring, a disk, a dome or a block. These shapes can be obtained by secondary process or tertiary process etc., of the collagen gel fragment.

Furthermore, in a preferred embodiment of the method of producing the collagen material according to the present invention, is characterized in that the method further comprises;

a step for introducing bubble into the collagen gel fragment, by means of any one method of a pressure-reduced pressure method, a gas-liquid shearing method and/or a method of introducing bubble using a membrane having a pore. At this moment, "introducing bubble" is for introducing oxygen. That is, it is for obtaining a collagen material containing oxygen. A merit of containing oxygen may be applied to and referred to the above explanation of the collagen material containing oxygen.

Although oxygen may include bubble, an embodiment of containing oxygen will be explained as follows. That is, containing of oxygen may be nearly equal to containing bubble. As the component, (1) in the case that it contains air (which is general air containing oxygen, nitrogen, carbon dioxide), (2) in the case that a low concentration or a high concentration of oxygen is contained in air (which also includes those of the content of the other components such as nitrogen or carbon dioxide being changed depending on increase and decrease of oxygen concentration.), (3) in the case that it contains only oxygen. It is though that there are at least the above three embodiments of containing oxygen.

in the similar way of the case of the addition of "cell growth promotant", it is for obtaining a condition that "bubble (the above air, or oxygen etc.)" is contained in the collagen gel fragment. Further, specifically, it is preferable to introduce bubble at a stage of preparing the collagen gen fragment, as these method, the following method can be explained with an example.

For example, a proportion of air is introduced into a vessel with a cover which a collagen solution is added, and is mechanically produced a vibration in the vessel after covered, and is gelated the collagen solution containing bubble. There is a possibility that a sufficient small bubble can not be obtained if air is just mixed into the collagen solution by producing a vibration in the vessel. Moreover, in the case that a small bubble such as so called nano bubble is needed, the following methods can be used.

For example, it is possible to introduce a smaller bubble than those of being made by shaking with hand or shaking mechanically, if air is added into the collagen solution, and then the solution is shook with ultrasonic wave etc.

Moreover, in a preferred embodiment according to the present invention, the method further comprises;

a step for introducing bubble into the collagen gel fragment, by means of any one method of a pressure-reduced pressure method, a gas-liquid shearing method and/or a method of introducing bubble using a membrane having a pore. At first, in the case of introducing a micro bubble will be explained. In the case of introducing a micro bubble, it is possible to introduce the bubble into the collagen material by using a pressure-reduced pressure method, or a gas-liquid shearing method. At first, the pressure-reduced pressure method will be explained. The pressure-reduced pressure method is a method wherein a large amount of air is dissolved under the conditions of adding a high pressure to produce bubble again by reducing the pressure. Moreover, a gas-liquid shearing method is a method wherein an eddy-current (400 to 600 revolutions per second) is produced, and air is sucked in the eddy-current, and the air is cut and grinded by a fan etc., to generate a lot of bubble. These methods can be applied to the present invention.

Moreover, it is possible to use a method of introducing bubble using a membrane having a pore, in the case that a smaller size of nano bubble than micro bubble is needed to introduce the collagen material. This method is a technology of applying pressure on gas and thereby emitting the gas from a membrane which countless numbers of nano level of hole is opened, to generate a nano bubble. As a membrane, a Shirasu Porous Glass (SPG) membrane is used. It is possible to introduce bubble, micro bubble, or nano bubble etc., into the collagen material according to these common procedure at a desired level.

As mentioned above, the process of the method is simply summarized as follows. That is, the prepared orientated collagen gel with a string shape is aligned at a desired shape. The align may be a plane shape or a three-dimensional shape obtained by laminating one or more layer. Moreover, a direction of a string shape in the plane shape or the three-dimensional shape is a direction of orientation. Therefore, the orientated collagen gel with a string shape can be linearly aligned in the case that a linearly orientation is needed, the orientated collagen gel with a string shape can be roundly aligned in the case that a roundly orientation is needed.

The dryness of the orientated collagen gel with a string shape makes it possible to firmly fix the collagen gel each other. In this way, a collagen material of the present invention can be obtained by the method of producing the collagen material according to the above present invention. That is, it is possible to obtain the orientated collagen material capable of freely designing a shape and a direction of orientation by means of using the orientated collagen gel with a string shape, and then aligning it to a plane shape or a three-dimensional shape such as a ribbon, a sheet, a tube, or a block, and after that drying it.

According to the manufacturing method according to the present invention, it is also possible to obtain the collagen material capable of freely designing a shape by means of using the collagen gel with a string shape, and then aligning it to a plane shape or a three-dimensional shape such as a ribbon, a sheet, a tube, or a block, and after that drying it, even if the collagen gel with a string shape has not orientation.

EXAMPLE

At this moment, the present invention will be concretely explained in more detail with reference to Examples, but the invention is not intended to be interpreted as being limited to Examples. Moreover, it is possible to change appropriately without departing from the scope of the invention.

Example 1

In a method of the present invention, first of all, a collagen gel was prepared as an orientated collagen (substrate) having a size of a millimeter order or more. As to a collagen gel, 9.3 mg/mL concentration of I type of collagen solution derived from a rat tail (BD Company) was extruded through a nozzle having 0.38 mm of an inside diameter into a plate container containing a phosphate buffered saline (PBS) at 38° C., at pH7.4, and thereby sliding the nozzle to obtain a string like collagen gel having about 1 mm in diameter, about 20 mm of length.

Figure 5:
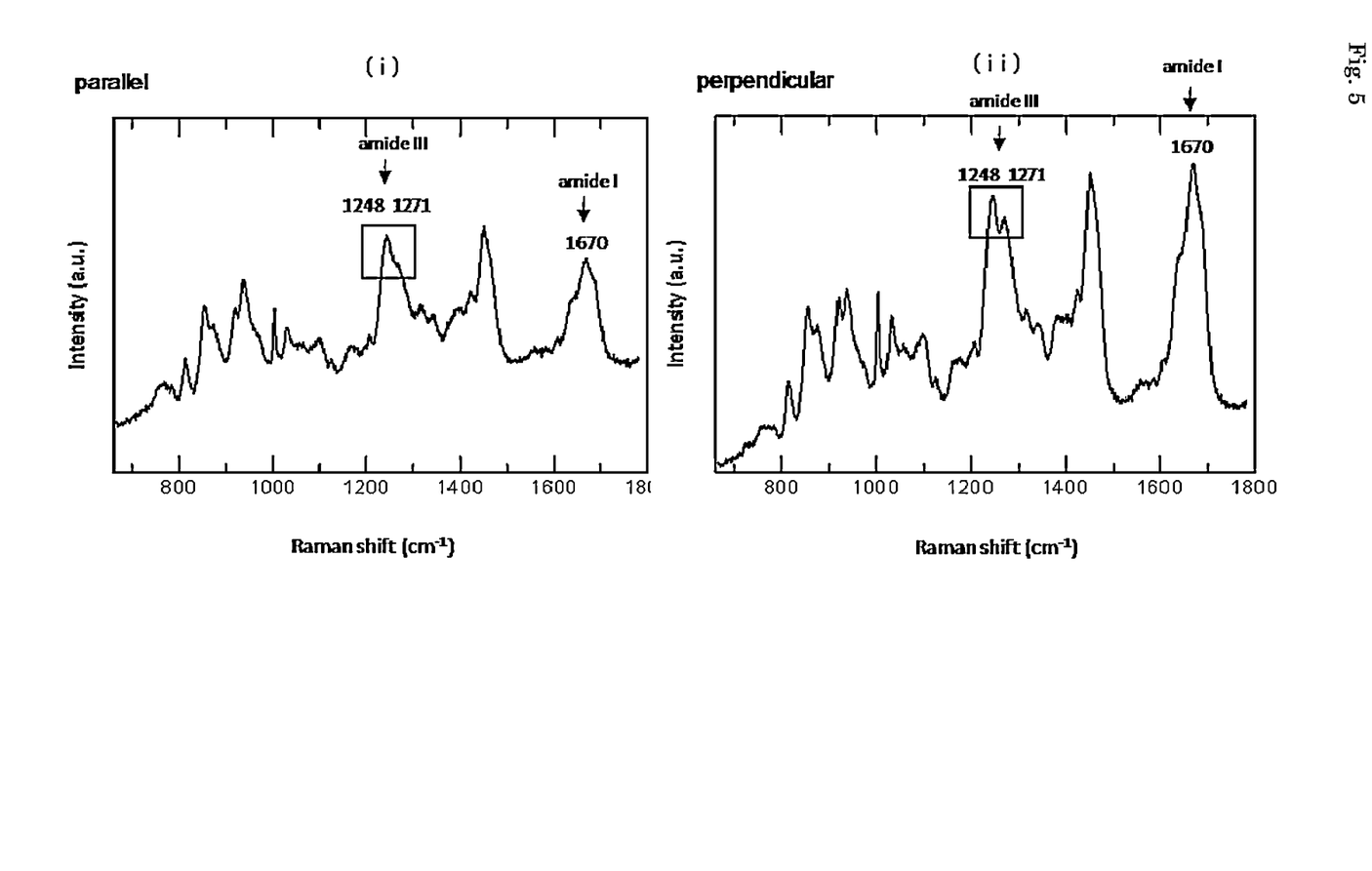
FIG. 5 gives a raman spectrum of an orientated collagen, (i) shows a spectrum in the case that a direction of a laser polarization is in parallel with a travel direction of a collagen, (ii) shows a spectrum in the case that a direction of a laser polarization is perpendicular to a travel direction of a collagen, respectively.

An orientation of a collagen gel obtained thus was analyzed by a raman spectroscopic microscope (PHOTON Design Corporation). In doing so, an excitation wavelength was set at 514.5 nm using a continuous oscillation argon ion laser Stabilite 2017 (Spectra-Physics, Inc.), a HR-320 (Jovin Yvon S.A.S.) as a spectroscope and a LN/CCD-1100-PB/UV AR/1 (Roper scientific Inc.) were used respectively. FIG. 5 gives a result of evaluating a strength of an amide I and an amide III in the case that a direction of a laser polarization is in parallel with and is perpendicular to a travel direction of a collagen. A peak derived from an amide I depends on a vibration of a C=O bonding located in a direction which is perpendicular to a collagen fiber, and a peak derived from an amide III depends on a vibration of a C—N bonding located in a direction which is in parallel with and perpendicular to a collagen fiber. According to FIG. 5, as to a spectrum wherein a direction of a laser polarization is in parallel with a travel direction of a collagen, compared with a strength of a peak depending on a $CH_3$ bending vibration around 1450 $cm^{-1}$, a peak strength of amide I (1670 $cm^{-1}$) as to a perpendicular direction was higher than that of a parallel direction. Further, in a spectrum wherein a direction of a laser polarization is perpendicular to a travel direction of a collagen, a peak of a vibration depending on a C—N bonding located in a direction perpendicular to a collagen fiber was observed around raman shift, 1270-1300 cm$^{-1}$. That is, it was recognized that a collagen fiber was oriented to a long axes direction of a collagen gel.

Example 2

Next, a larger size of the collagen material is tried to obtain. First of all, a orientated collagen gel with a string shape was prepared. As to a collagen gel, 9.3 mg/mL concentration of I type of collagen solution derived from a rat tail (BD Company) was extruded through a nozzle having 0.38 mm of an inside diameter into a plate container containing a phosphate buffered saline (PBS) at 38° C., at pH7.4, and thereby sliding the nozzle to obtain a string like collagen gel having about 1 mm in diameter, about 200 mm of length. FIG. 1 gives a photograph of an orientated collagen gel with a string shape immediately after it is produced in PBS.

Figure 2:
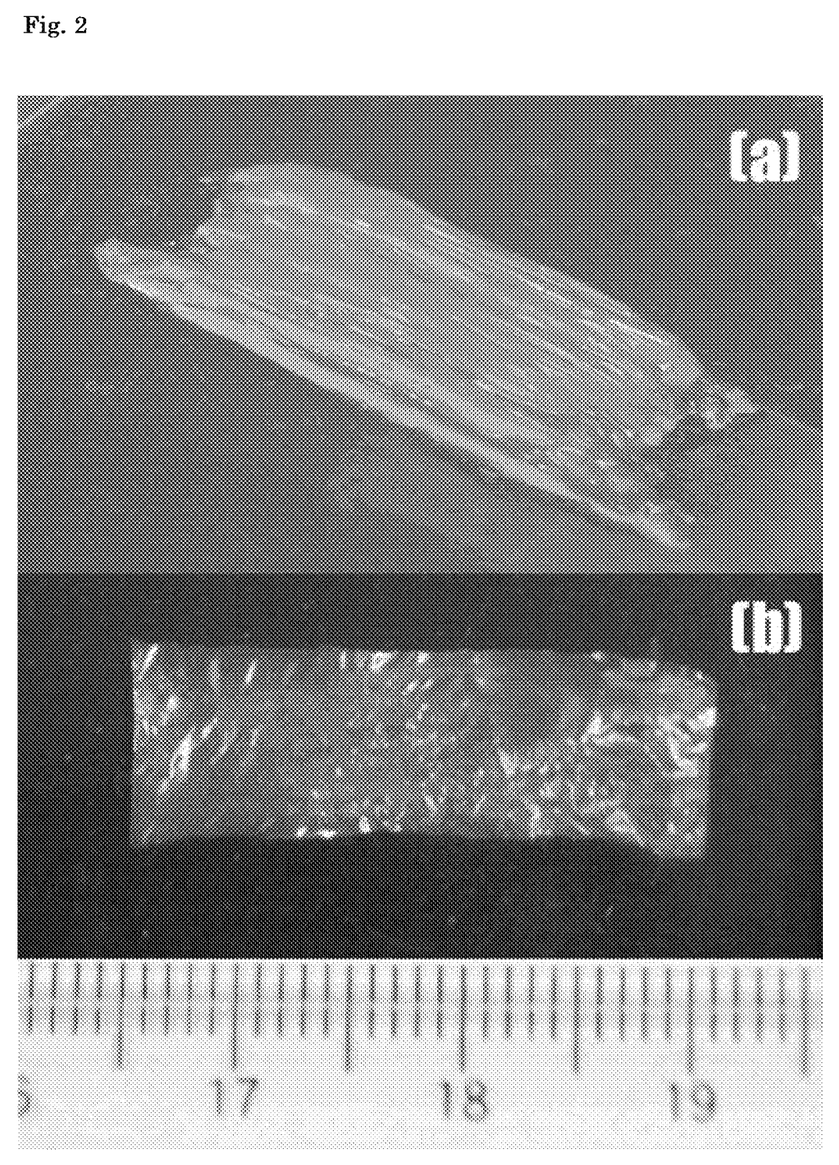
FIG. 2 gives a photograph of a dried orientated collagen material (FIG. 2(b)) with a ribbon shape obtained by drying after an orientated collagen gel with a string shape is aligned to a ribbon shape (FIG. 2(a). An orientation of the ribbon shape in inside of sample is in parallel with a travel direction of an orientated collagen with a string shape.

The produced orientated collagen gel with a string shape is aligned on a plane as shown in FIG. 2, and after that is dried to obtain a dried orientated collagen material with a sheet shape.

Example 3

Figure 3:
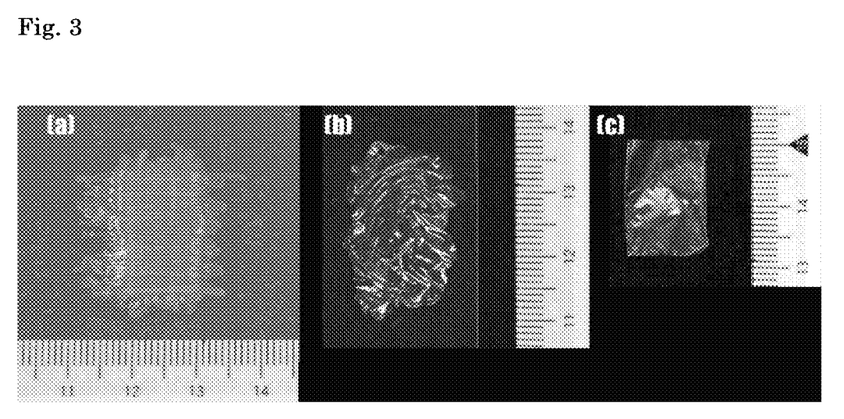
FIG. 3 gives a photograph in the case that an orientated collagen gel with a string shape is aligned to two layers (FIG. 3(a)), and a first layer and a second layer are perpendicular as to a travel direction of an orientated collagen with a string shape.

The above mentioned orientated collagen gel with a string is aligned on the plane with a sheet shape. After that, a second layer is aligned wherein a direction of an orientated collagen gel with a string shape is perpendicular to a travel direction of the orientated collagen with a string shape of the first layer (FIG. 3(*a*)). After that, a dried sample is shown in FIG. 3 (*b*), a sample cut in rectangles after drying is shown in FIG. 3 (*c*). In this way, it is possible to make not only single layer but multiple layers using the orientated collagen sheet with a sheet shape, and further it is possible to freely design a direction of orientation of each layer.

Example 4

Figure 4:
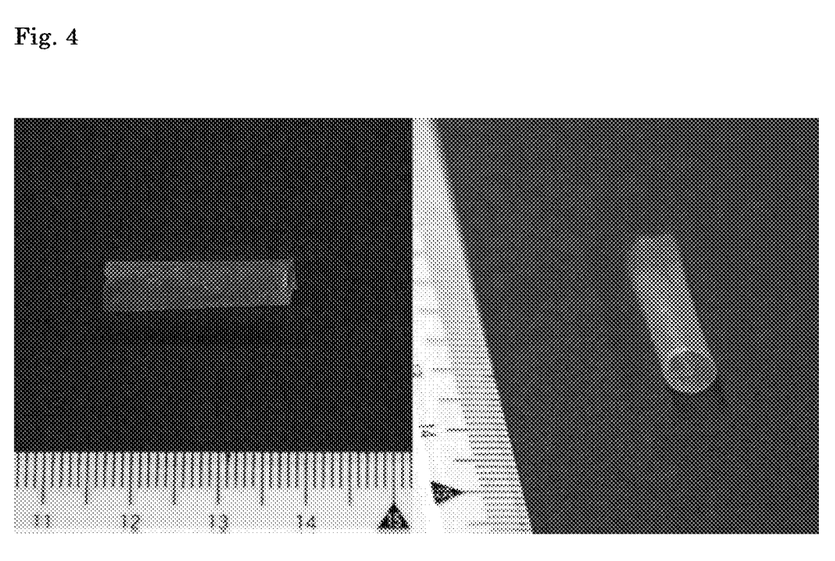
FIG. 4 gives a photograph of a dried orientated collagen material with a tube shape made by obtaining a sheet shape using an orientated collagen gel with a string shape, and after that, winding the sheet for an axle rod, and removing the axle rod from the sheet.

The above mentioned orientated collagen gel with a string shape was designed on a plane to make a sheet shape, and after that, was dried. After that, the obtained sheet is winded for an axle rod, and the axle rod is removed from the sheet to obtain a dried orientated collagen material with a tube shape (FIG. 4). It is possible to freely design a direction of orientation of the collagen material with a tube shape depending on a direction of winding a sheet having orientation to the axle rod, since a direction of orientation of the collagen material with a sheet shape is equal to a travel direction of the orientated collagen with a string shape. That is, it is possible to freely design an angle to a direction such as a direction of a tube axial, a circumferential direction of a tube, or from a direction of a tube axial.

Further, it is possible to freely design a diameter of a tube according to a size of the axle rod. Further, it is possible to make multiple layers of the collagen material with a tube shape and to freely design a direction of orientation in each layer of these multiple layers.

Example 5

Figure 6:
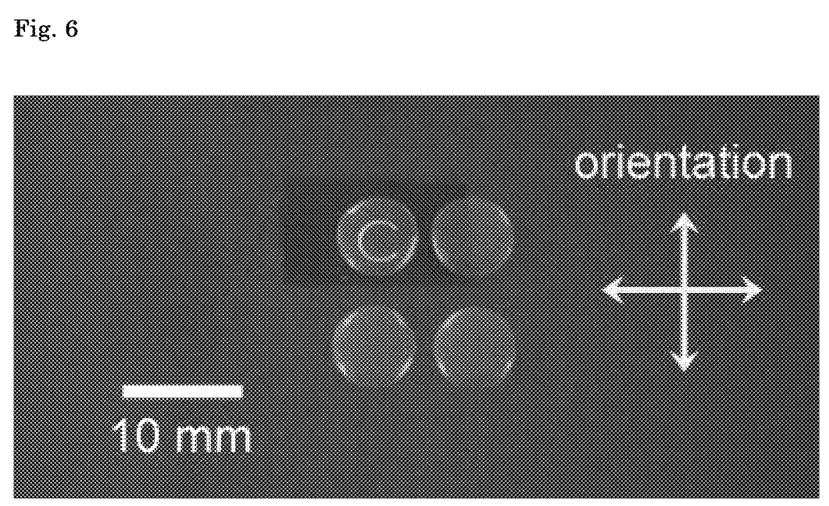
FIG. 6 gives an example of a dome type of the collagen material.

Next, it was tried to produce a dome type of the collagen material. FIG. 6 gives an example photograph of a dome type of the collagen material. A dimension is not measurement, but scale display. Although FIG. 6 gives a photograph at the time of drying, in order to emphasize a transparency, among four sheet samples in a black back ground of one sheet sample a white character "C" is set. The four sheets consist of 20 layers wherein a direction of orientation is perpendicularly intersected with every layer. Moreover, in figure, a yellow arrow shows a direction of orientation. In figure, although it is recognized that there are some reflection in the outside of a dome which is looked like a circle, this shows that the reflecting light can be observed since it is a circle as well as a dome type. That is, although the above material having 20 layers is itself "three-dimensional structure" of the collagen sheet, further, it is recognized that it is possible to make (and dry) not only a flat disk type using these 20 layers, but also a dome type, and therefore, it is also possible to make more "complicated three-dimensional structure". This dome type of the sample is aimed to the regeneration of cornea, and thereby these curvature making consistent with a curvature of eyes.

In this way, it is recognized that it is possible to produce a wide various sort of shape according to the collagen material of the present invention, and to make a meaningful contribution to a regeneration medicine.

Figure 7:
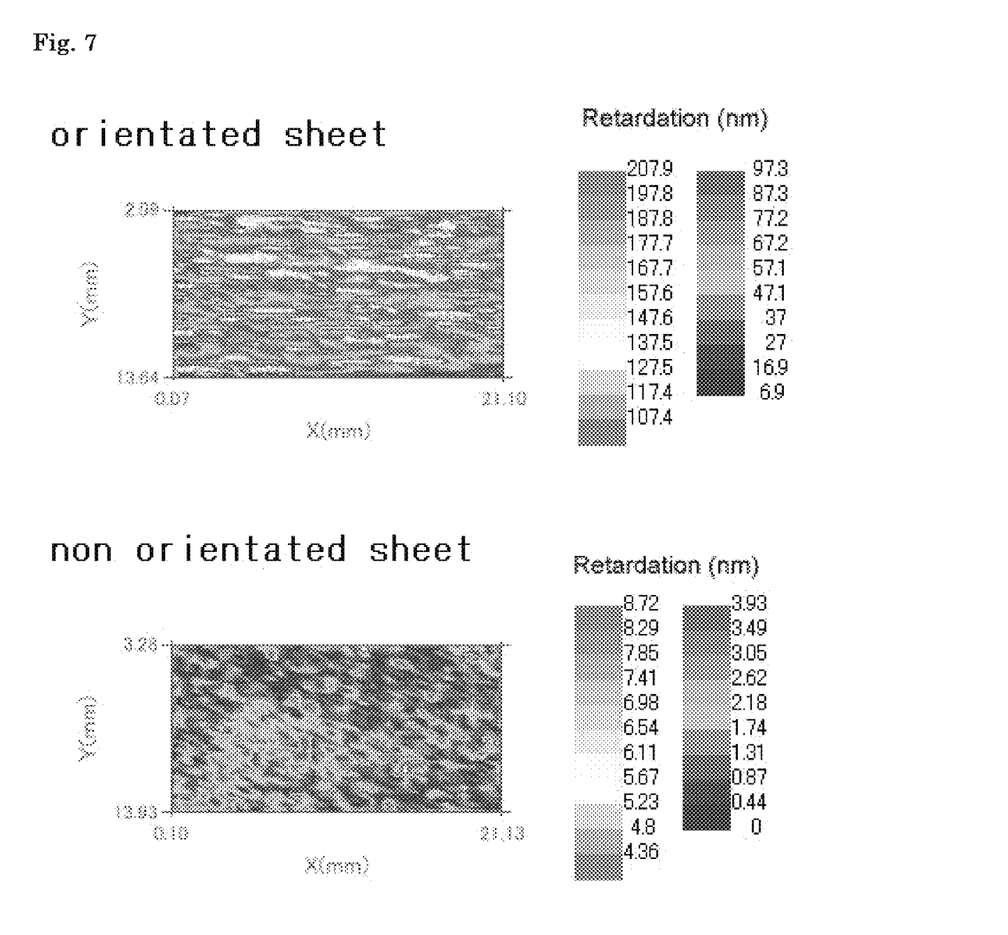
FIG. 7 gives a result that an orientation test is performed as to the orientated sheet and non orientated sheet.

Moreover, the orientation of the collagen material with a sheet shape was evaluated with other measuring method. FIG. 7 gives a result that an orientation test is performed as to the orientated sheet and non orientated sheet. That is, this is a figure shows that both orientation of dried orientated collagen sheet and dried non orientated collagen sheet produced by the above method of producing the collagen material is quantitatively evaluated. Both thicknesses of the sheets was about 10 micrometer. This figure shows evaluation of the "phase difference" in the samples according to an ellipsometry devise using a parallel nicol rotation method. The Retardation in the figure means a phase difference, a phase difference in a rectangular sheet is shown in the contour map. It is recognized that this phase difference in the case of the orientated sheet is higher than that of non orientated sheet, and further a direction of the contour map increases in length from side to side (Although it is difficult to recognize, in the orientated sheet, a red-tinged part showing 187.8 to 207.9 nm is observed in several part, while in non orientated sheet these are almost never observed in the same region. Moreover, in the orientated sheet, a yellow part showing 127.5 to 147.6 nm is recognized in a lot of region (about 10 to 20% region of total region), while in non orientated sheet these are only observed in a slight amount of region in several part. In non orientated sheet, almost region become a blue to a dark green region showing 0 to 3.93 nm.). A direction from side to side in figure is a direction of orientation of the orientated collagen, that is, a direction wherein a string having orientation is aligned.

INDUSTRIAL APPLICABILITY

The present inventions make it possible to contribute to a therapy for disorder and a regenerative medicine and dental fields (in particular, orthopaedic surgery, a cerebral surgery, a medical dentistry) and basic medical fields. Moreover, it is possible to freely design a collagen material having an orientation according to these site existing in vivo of human, and to contribute to a regenerative medicine and basic medical fields.

The invention claimed is:

1. A method of producing a collagen material, wherein the method comprises:

a step for preparing string collagen gels formed and orientated by extruding collagen solution through a nozzle into a container containing a phosphate buffered saline (PBS) solution, and providing a flow of a fixed direction to a collagen solution, wherein a shape of each of the string collagen gels is a string and a direction of an orientation of each of the string collagen gels is a direction of the string shape, a step for obtaining multiple string collagen gels wherein an orientation of the multiple string collagen gels is controlled, a step for arranging the multiple string collagen gels in a desired shape, a step for drying the multiple string collagen gels arranged in the desired shape to couple the multiple string collagen gels to each other, and a step for introducing a bubble into the string collagen gels by means of at least one of a pressure-reduced pressure method, a gas-liquid shearing method, and a method of introducing a bubble using a membrane having a pore.

2. A method of producing a collagen material according to claim 1, wherein the desired shape is at least one of a planar shape and a three-dimensional shape.

3. A method of producing a collagen material according to claim 1, wherein the desired shape is a ribbon, a sheet, a tube, a rod, a ring, a spiral, a disk, a dome or a block.

4. A method of producing a collagen material according to claim 1, wherein the step for drying the string collagen gels is carried out by freeze dry.

* * * * *